United States Patent [19]

Ruderman

[11] 4,431,410
[45] Feb. 14, 1984

[54] UNIVERSAL FACEBOW

[76] Inventor: Howard J. Ruderman, 86 Shrub Hollow Rd., Roslyn, L.I., N.Y. 11576

[21] Appl. No.: 337,580

[22] Filed: Jan. 7, 1982

[51] Int. Cl.³ .............................................. A61C 7/00
[52] U.S. Cl. ........................................................ 433/5
[58] Field of Search .................................... 433/6, 5, 7

[56] References Cited

U.S. PATENT DOCUMENTS

| | | | |
|---|---|---|---|
| 1,103,606 | 7/1914 | Monteg | 433/5 |
| 4,202,100 | 5/1980 | Foster | 433/5 |
| 4,268,250 | 5/1981 | Reeve | 433/20 |

Primary Examiner—Robert Peshock
Attorney, Agent, or Firm—Robert W. Fiddler

[57] ABSTRACT

A facebow for use in orthodontic procedures is provided with relatively universal adjustability to permit use of a single size of facebow in mouths of a variety of different sizes and further facilitating selective unilateral movement. To this end, the facebow is formed with a conventional outer bow for securement to a cervical elastic strap or head gear; and an inner bow contoured to fit into the mouth of the patient along the dental arch, preferably approximating the molars. The inner bow is secured to the outer bow, and the inner bow is formed with at least a pair of mesial loops arranged to lie along the surface of the teeth over which the inner bow is positioned. These loops provide the four-fold function of (1) providing means for the dentist to adjust the effective length of the inner bow by increasing or decreasing the curvature of the loop; (2) permitting selective unilateral pressure to be applied to the dental arch; (3) providing an added variable site for affixing auxiliary attachments, such as hooks and springs; and (4) providing a finger engaging seat to facilitate facebow manipulation. Additional adjusting loops may be arranged along the inner archwire, again oriented in the plane of the wire along the teeth against which the inner bow is positioned, extending either upwardly or downwardly with respect to the wire. The loops are preferably formed of a height between 30% and 300% of the tooth height or "clinical crown," and a spacing between the legs of the loop between 25% and 150% of loop height.

10 Claims, 2 Drawing Figures

UNIVERSAL FACEBOW

BACKGROUND OF THE INVENTION

This invention relates to the art of orthodontics, and more particularly to an improved orthodontic facebow and method for applying facebows in orthodontic procedures, facilitating the use of a single size of facebow for most patients.

Among the appliances evolved for effecting desired orthodontic corrections, a so-called "facebow" has been evolved in which an inner bow is provided for positioning along the upper or lower teeth of the patient, so as to provide means for applying desired forces to these teeth to effect desired orthodontic action. The application of force to the teeth via the inner bow is obtained by connecting the inner bow to an outer bow, extending along the cheeks of a patient and coupled to a head or cervical gear, such for example as an elastic member stretched over the rear of the head or neck respectively of the patient. The inner bow is coupled to the teeth by extending the ends of the relatively U-shaped inner bow through retaining tubes attached to the teeth of the patient, and by means of hooks on the outer bow to the head gear or cervical gear.

Such extra-oral force facebows are widely used. Among the problems arising in their use, is that the orthodontist is required to stock an inventory of a variety of differently sized facebows to accommodate a great variety of different patients to whom the facebows are to be applied. Aside from the increase in cost resulting from the need to maintain an inventory of differently sized facebows, the delay in selecting a properly sized facebow, and the increased storage facility which must be provided, the use of standard size bows does not necessarily result in a precise desired fitting of the inner bow to the teeth of the patient, since there may not be a precise corelationship between the dimensions of the facebows in stock and the arch of the patient's mouth.

Further, in positioning the facebow, it is necessary to guide the free ends of the inner bow into the molar retaining tubes. The dentist positioning the archwire generally has no problem since he can see what he is doing. However, facebows are generally intended for use in the privacy of the home, since the appearance of the facebow and associated cervical or head band is not generally regarded as esthetically acceptable in most social situations. The patient thus must apply and remove the facebow. Patients often find it difficult to manipulate the bow into desired position on the teeth, since they must be either working by feel or by a mirror image, and find it difficult to guide the free ends of the inner bow into the molar tubes.

It is with the above problems in mind that the present improved facebow has been evolved, serving to permit a single size of facebow to be employed almost universally on different patients, and further to facilitate the ease with which the facebow may be applied and removed by orthodontist and patient.

It is accordingly among the primary objects of the invention to provide an improved facebow design which may be applied relatively universally in patients of different oral dimensions.

A further object of the invention is to provide a facebow design that can minimize the inventory maintenance requirements of an orthodontist.

Another object of the invention is to provide an improved facebow which can be relatively easily positioned in the mouth of the wearer either by the orthodontist or the patient.

Another object of the invention is to provide an improved facebow which can be readily adjusted as the desired correction takes place, without requiring the use of different additional facebows.

An additional object of the invention is to allow the orthodontist greater flexibility in treatment strategies by increasing availability of placement sites for corrective attachments.

A further object of the invention is to provide a facebow permitting the selective application of unilateral pressure to the dental arch of the patient.

BRIEF DESCRIPTION OF THE INVENTION

These and other objects of the invention which will become hereafter apparent are achieved by forming a facebow with an outer bow of conventional relatively U-shaped configuration with the length of the bow dimensioned to extend back over the cheeks of the patient, and these ends formed with hooks adapted for engagement with the ends of an elastic cervical band or headgear which extends over the head or neck of the wearer and exerts an elastic pull on this outer bow. An inner bow is attached to the outer bow either by a fixed or swivel connection, and this inner bow is contoured generally to the arch of the maxillary teeth. This inner bow is secured to the inner maxillary teeth by engaging the free end of the U-shaped inner bow in molar retaining tubes which are cylindrical tubes secured to the face of the molars. According to the invention, a loop is formed in the inner bow to lie in the plane alongside the teeth over which the inner bow is positioned. At least one mesial loop is arranged along each arm of the inner bow, with this inner bow loop serving the fourhold function (1) permitting adjustment of inner bow length by increasing or decreasing the radius of curvature of the loop; (2) providing sites for the attachment of hooks and/or springs; and (3) provide a finger engaging grip; and (4) permitting selective application of arch pressure by bending the loop on one side more than on the other. Additional mesial loops are preferably provided spaced from the first described loop to further increase the range of adjustability of the inner bow, with these additional loops also lying the plane running parallel to the teeth surfaces over which the inner bow is positioned.

A feature of the invention resides in the fact that by the relatively simple expedient of forming the inner bow with loops, universal adjustability and manipulability of the facebow is significantly improved.

BRIEF DESCRIPTION OF THE DRAWINGS

The particular details of the invention, and the best mode contemplated for carrying out the invention and of the manner and process of making the invention, will be described in full, clear, concise and exact terms, in conjunction with the accompanying drawings, wherein.

DESCRIPTION OF PREFERRED EMBODIMENT

Figure 1:
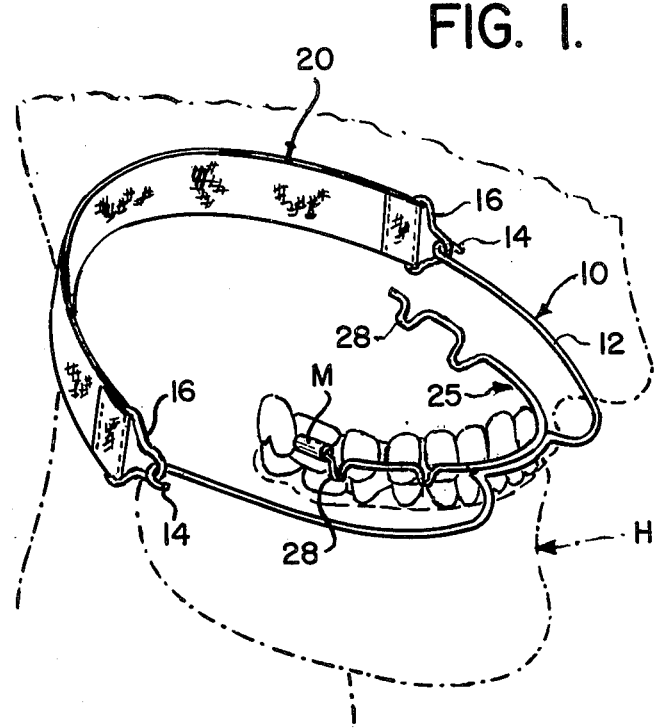
FIG. 1 is a perspective view showing the improved archwire in position on the head of a patient, the outline of which is shown in dot-dash lines, with the archwire operatively positioned over the upper teeth of the patient, and the teeth on the right-hand side drawn in, while those on the left are not shown.

As best seen in the drawings, the improved facebow 10 is formed with an outer bow 12 contoured to fit over the cheeks of the wearer, and formed with terminal hooks 14 adapted to engage attaching rings 16 on the illustratively shown elastic strap 20, which as seen in FIG. 1 is dimensioned to fit about the back of the neck of the patient.

Figure 2:
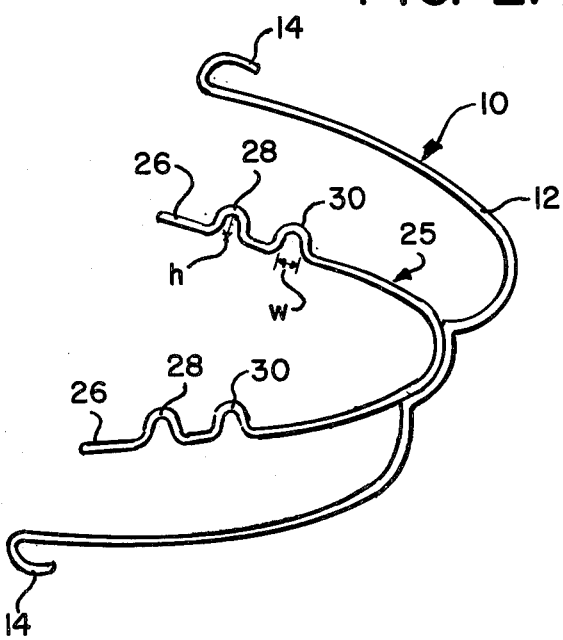
FIG. 2 is a top perspective view of an archwire embodying the invention, showing the adjusting loops extending upwardly.

Secured to the outer bow 10 is inner bow 25, as seen in FIG. 2, contoured to fit over the dental arch of the patient as seen in FIG. 1, and approximating the molars "M." The inner bow 25 is formed with linearly extending ends 26, as best seen in FIG. 2, adapted for insertion in molar retaining tubes "M," as best seen in FIG. 1. At the forward end of the molar retaining tubes "M," a distal loop 28 is formed. In accordance with a preferred embodiment of the invention, as illustrated, a second set of loops 30 are mesially arranged between loops 28 and the front of inner bow 25. Loops 28 and 30 are formed in the inner bow to extend in a plane adjacent the face of the tooth along which the inner bow will lie, and these loops are preferably dimensioned to extend no further from the linear axis of the inner bow than one centimeter more than the distance between the inner bow axis and the gum line. Further, the loop is formed preferably with a width between 25% and 150% of its height, with a height of 100% of typical tooth height. Thus, with a typical tooth height of between 5 and 12 mm., loop heights of between 4 and 15 mm. are desirable. Loop widths between 3-20 mm. are found acceptable.

OPERATION

The aforedescribed improved facebow 10 is fabricated employing conventional metal fabricating techniques bending conventionally employed orthodontic wire into the illustrated configuration. A variety of stainless steels may conveniently be employed, such as a 304 stainless steel wire, with the outer bow 12 having a diameter between 0.05" and 0.075" and the inner bow formed of a stainless steel having a diameter between 0.04" and 0.06", with a reduced diameter linear end 26.

The inner bow 25 is joined to the outer bow 12 by conventional metal joining techniques, such as welding or hot soldering, and may, if desired, be hingedly connected.

In use, the facebow 10 is adapted to the mouth of the patient by the dentist, who has initially applied desired molar retaining tubes "M," as seen in FIG. 1, anchored to the molars of the patient. The facebow is applied to the patient by dimensioning the inner bow 25 to approximate the dental arch of the patient by distending or compressing loops 28 and 30. The linear free ends 26 of the inner bow are positioned as conventionally in the tubes "M," and the hooks 14 on the free end of outer bow 12 are secured to the cervical elastic strap or headband 20.

In the event that it is desired to apply unilateral force to one side of the dental arch to effect unilateral movement of teeth, the loops 28 and 30 are contracted on one side of the inner bow and expanded on the other side.

Attachments may additionally be secured to the mesial loops 30, as desired.

The loops 28 and 30 are formed in the inner bow in a fashion so as to lie in a plane between the gum and the inner cheek adjacent the teeth about which the inner bow is positioned. These loops may extend either upwardly or downwardly from the inner bow, so as to provide maximum comfort to the patient. Distal loops 28 are preferably arranged at a point adjacent linear ends 26, so as to limit the movement of the linear ends 26 into the retaining tubes "M."

It is thus seen that a simple, effective facebow has been provided which may be formed of a single dimension and subsequently adjusted by the dentist to accommodate differently sized mouths, and further to permit the selective application of unilateral forces.

The above disclosure has been given by way of illustration and elucidation, and not by way of limitation, and it is desired to protect all embodiments of the herein disclosed inventive concept within the scope of the appended claims.

What is claimed is:

1. An orthodontic facebow permitting the orthodontic practitioner to stock a single size of facebow for use on patients having a wide variety of different mouth sizes, said facebow comprising:
   an outer bow contoured to extend over the cheeks of the patient;
   attaching means on the free ends of said outer bow adapted for securement to a cervical strap or head gear;
   an inner bow of relatively non-spring material secured to said outer bow at a point approximating the centers of said inner and outer bows, said inner bow contoured to approximate the dental arch of the patient; and
   a plurality of loops, at least one on each side of the inner bow, said loops lying in a plane parallel to the faces of the teeth along which the inner bow is arranged, and not impinging on any soft tissue in the mouth of the patient, said loops being selectively compressible or expandable to increase or decrease the length of the inner bow to a length approximating the dental arch of the patient with at least one of said loops lying at least one-half the length of the inner bow from its front, and one or more of the loops on one side of the bow being wider spaced than those on the other side of the bow whereby the bow is shifted to one side to effect unilateral correction.

2. An orthodontic facebow as in claim 1 in which said plurality of loops include: a pair of distal loops, one of the pair arranged adjacent each linearly extending end of said inner bow.

3. An orthodontic facebow as in claim 2, in which said plurality of loops include a pair of mesial loops, one of which is arranged on each leg of said inner bow.

4. An orthodontic facebow as in claim 1, in which said loops are of a height between 30% and 300% of the height of a tooth in connection with which the facebow is to be employed.

5. An orthodontic facebow as in claim 1, in which said loops are formed with a width between the legs of the loop between 25% and 150% of loop height.

6. A method of forming an orthodontic facebow to permit utilization of a single size of facebow on patients having a wide variety of different mouth sizes and to permit unilateral correction, said method comprising the steps of:
   forming a facebow with an outer bow contoured to extend over the cheeks of the patient;
   providing attaching means on the free ends of the outer bow;

forming an inner bow of relatively non-spring material contoured to approximate the dental arch of the patient;

securing the inner bow to the outer bow at a point approximately the centers of the inner and outer bows;

forming a plurality of loops at least one on each side of the inner bow in a plane lying parallel to the face of the teeth along which the inner bow is to be arranged; with at least one of said loops lying at least one-half the length of the inner bow from its front, and one or more of the loops on one side of the bow being wider spaced than those on the other side of the bow whereby the bow is shifted to one side to effect unilateral correction and selectively compressing or expanding at least one of the loops to increase or decrease the length of the inner bow to a length permitting the inner bow to approximate the dental arch of the patient.

7. A method as in claim 6, in which the step of forming a plurality of loops includes the steps of forming a pair of distal loops, one of each pair arranged adjacent each end of the outer bow.

8. A method as in claim 7, in which the step of forming a plurality of loops includes the steps of forming a pair of mesial loops one of which is arranged along each leg of the inner bow.

9. A method as in claim 6, in which the loops are formed of a height between 30% and 300% of the height of a tooth in connection with which the facebow is to be employed, and the width of the loops is between 25% and 150% of the loop height.

10. A method of applying an orthodontic facebow having an inner bow and outer bow of relatively non-spring material, with free ends on each, to a patient, said method comprising the steps of:

forming a plurality of loops in the inner bow; with at least one of said loops lying at least one-half the length of the inner bow from its fronts, and one or more of the loops on one side of the bow being wider spaced than those on the other side of the bow whereby the bow is shifted to one side to effect unilateral correction;

compressing or distending a loop to increase or decrease the length of the inner bow to cause the inner bow to be of a length approximate the dental arch of the patient;

bending the outer bow to extend over the cheeks of the patient;

applying attaching tubes to at least two teeth on opposed sides of the jaw of the patient;

inserting the free ends of the inner bow one in each attaching tube; and extending an elastic band about the head of the patient from the free ends of the outer bow.

* * * * *